(12) United States Patent
Fu

(10) Patent No.: US 12,358,834 B2
(45) Date of Patent: Jul. 15, 2025

(54) GLASS-CERAMICS BASED ON LITHIUM DISILICATE, ZIRCON, AND APATITE

(71) Applicant: Corning Incorporated, Corning, NY (US)

(72) Inventor: Qiang Fu, Painted Post, NY (US)

(73) Assignee: CORNING INCORPORATED, Corning, NY (US)

( * ) Notice: Subject to any disclaimer, the term of this patent is extended or adjusted under 35 U.S.C. 154(b) by 1013 days.

(21) Appl. No.: 17/422,890

(22) PCT Filed: Jan. 7, 2020

(86) PCT No.: PCT/US2020/012491
§ 371 (c)(1),
(2) Date: Jul. 14, 2021

(87) PCT Pub. No.: WO2020/150041
PCT Pub. Date: Jul. 23, 2020

(65) Prior Publication Data
US 2022/0089473 A1    Mar. 24, 2022

Related U.S. Application Data

(60) Provisional application No. 62/793,071, filed on Jan. 16, 2019.

(51) Int. Cl.
*C03C 4/00* (2006.01)
*C03C 10/00* (2006.01)
*C12N 5/077* (2010.01)

(52) U.S. Cl.
CPC ........ *C03C 4/0007* (2013.01); *C03C 10/0027* (2013.01); *C12N 5/0654* (2013.01); *C12N 2500/12* (2013.01)

(58) Field of Classification Search
CPC . C03C 4/0007; C03C 10/0027; C12N 5/0654; C12N 2500/12
See application file for complete search history.

(56) References Cited

U.S. PATENT DOCUMENTS

| | | | |
|---|---|---|---|
| 6,802,894 B2 | 10/2004 | Brodkin et al. | |
| 11,845,689 B2* | 12/2023 | Christiansen | B65D 1/40 |
| 2011/0136651 A1 | 6/2011 | Yagi et al. | |
| 2015/0087493 A1 | 3/2015 | Ritzberger et al. | |

(Continued)

FOREIGN PATENT DOCUMENTS

| | | |
|---|---|---|
| CN | 101462829 A | 6/2009 |
| CN | 104379113 A | 2/2015 |

(Continued)

OTHER PUBLICATIONS

Chinese Patent Application No. 202080009484.X, Office Action dated Nov. 25, 2022, 4 pages (English Translation only), Chinese Patent Office.

(Continued)

*Primary Examiner* — Amber R Orlando
*Assistant Examiner* — Cameron K Miller
(74) *Attorney, Agent, or Firm* — Travis B. Gasa

(57) ABSTRACT

A glass-ceramic composition includes a first crystalline phase including lithium disilicate; and a second crystalline phase comprising at least one of: zircon, zirconia, apatite, or a combination thereof.

19 Claims, 3 Drawing Sheets

(56) References Cited

U.S. PATENT DOCUMENTS

| | | | | |
|---|---|---|---|---|
| 2016/0051349 A1* | 2/2016 | Rheinberger | ...... | A61C 13/0835 |
| | | | | 156/196 |
| 2016/0236971 A1* | 8/2016 | Rampf | ...... | C03C 10/16 |
| 2016/0257607 A1 | 9/2016 | Ritzberger et al. | | |
| 2017/0342383 A1* | 11/2017 | Deng | ...... | C03C 3/097 |
| 2019/0048318 A1 | 2/2019 | Deng et al. | | |
| 2022/0402809 A1* | 12/2022 | Coon | ...... | C03C 10/00 |

FOREIGN PATENT DOCUMENTS

| | | | |
|---|---|---|---|
| CN | 105121373 A | 12/2015 | |
| CN | 105683110 A | 6/2016 | |
| WO | 2017/205596 A1 | 11/2017 | |
| WO | 2017/223561 A1 | 12/2017 | |
| WO | WO-2017223551 A1 * | 12/2017 | ............. A61K 6/024 |
| WO | 2019/108571 A1 | 6/2019 | |

OTHER PUBLICATIONS

Apel et al., "Influence of ZrO2 on the crystallization and properties of lithium disilicate glass-ceramics derived from a multi-component system", J Eur Ceram Soc, 2007, 27:1571-1577.

Hallmann et al., "Effect of microstructure on the mechanical properties of lithium disilicate glass-ceramics", Journal of the Mechanical Behavior of Biomedical Materials, 2018. 82: p. 355-370.

Hannink et al, "Transformation toughening in zirconia-containing ceramics", Journal of the American Ceramic Society, 2000. 83(3): p. 461-487.

Hench et al., "Bioceramics", Journal of the American Ceramic Society, 1998. 81(7): p. 1705-1728.

Montazerian et al., "History and trends of bioactive glass-ceramics", Journal of Biomedical Materials Research Part A, 2016. 104(5): p. 1231-1249.

Qiang Fu et al., "Nature-inspired design of strong, tough glass-ceramics", MRS Bulletin, 2017. 42(3): p. 220-225.

International Search Report and Written Opinion of the International Searching Authority; PCT/US2020/012491 ; Mailed on Apr. 21, 2020; 10 Pages; European Patent Office.

English Abstract of: Mori et al., "Mechanical Properties of High Purity Sintered ZrSiO4", Journal of the Ceramic Society of Japan, 1990. 98(1141): p. 1017-1022.

* cited by examiner

GLASS-CERAMICS BASED ON LITHIUM DISILICATE, ZIRCON, AND APATITE

This application claims the benefit of priority under 35 U.S.C. § 371 of International Application Serial No. PCT/US2020/012491, filed on Jan. 7, 2020, which claims the benefit of priority under 35 U.S.C. § 119 of U.S. Provisional Application Ser. No. 62/793,071, filed on Jan. 16, 2019, the contents of both of which are relied upon and incorporated herein by reference in their entirety.

This application claims the benefit of priority under 35 U.S.C. § 119 of U.S. Provisional Application Ser. No. 62/793,071, filed on Jan. 16, 2019, the content of which is relied upon and incorporated herein by reference in its entirety.

BACKGROUND

1. Field

The disclosure relates to glass-ceramic compositions, bioactive glass-ceramic compositions, articles made from the glass-ceramic compositions, and to methods of making and using the bioactive glass-ceramic compositions and articles.

2. Technical Background

Strong, tough materials are in significant demand for the biomedical industry, where novel functional materials are needed for regenerating bone and teeth. Glass-ceramics based on lithium disilicate, apatite, and wollastonite offer desired mechanical properties, such as high body strength and fracture toughness.

This disclosure presents improved glass-ceramic compositions and methods of manufacturing thereof for biomedical applications.

SUMMARY

In some embodiments, a glass-ceramic composition comprises: a first crystalline phase including lithium disilicate; and a second crystalline phase comprising at least one of: zircon, zirconia, apatite, or a combination thereof.

In one aspect, which is combinable with any of the other aspects or embodiments, the second crystalline phase further comprises at least one of: β-spodumene, β-quartz, lithium aluminum phosphate, lithiophosphate, wollastonite, cristobalite, or a combination thereof.

In one aspect, which is combinable with any of the other aspects or embodiments, the apatite comprises at least one of: fluorapatite, hydroxyapatite, carbonated apatite, or a combination thereof.

In one aspect, which is combinable with any of the other aspects or embodiments, the first crystalline phase and the second crystalline phase, in combination, comprise a source of: 50 to 75 wt. % $SiO_2$, 1 to 5 wt. % $Al_2O_3$, 0.5 to 10 wt. % $P_2O_5$, 1 to 15 wt. % CaO, 5 to 20 wt. % $Li_2O$, 0 to 5 wt. % $Na_2O$, 0.5 to 20 wt. % $ZrO_2$, and 0.1 to 1.0 wt. % $F^-$, based on a 100 wt. % total of the composition.

In one aspect, which is combinable with any of the other aspects or embodiments, the first crystalline phase and the second crystalline phase, in combination, further comprise a source of: 0 to 10 wt. % $B_2O_3$, and 0 to 4 wt. % $K_2O$, based on a 100 wt. % total of the composition.

In one aspect, which is combinable with any of the other aspects or embodiments, the composition has a high fracture toughness in a range of 2.0 to 3.5 MPa·m$^{1/2}$.

In one aspect, which is combinable with any of the other aspects or embodiments, the composition has a high strength in a range of 200 to 500 MPa.

In one aspect, which is combinable with any of the other aspects or embodiments, the composition a high fracture toughness in a range of 2.0 to 3.5 MPa·m$^{1/2}$ and a high strength in a range of 200 to 500 MPa.

In one aspect, which is combinable with any of the other aspects or embodiments, the first crystalline phase and the second crystalline phase, in combination, comprise a source of: 55 to 70 wt. % $SiO_2$, 1 to 3 wt. % $Al_2O_3$, 2 to 6 wt. % $P_2O_5$, 4 to 8 wt. % CaO, 10 to 15 wt. % $Li_2O$, 0.1 to 1 wt. % $Na_2O$, 3 to 15 wt. % $ZrO_2$, and 0.2 to 0.8 wt. % $F^-$, based on a 100 wt. % total of the composition.

In one aspect, which is combinable with any of the other aspects or embodiments, the first crystalline phase and the second crystalline phase, in combination, further comprise a source of: 0 to 10 wt. % $B_2O_3$, and 0 to 4 wt. % $K_2O$, based on a 100 wt. % total of the composition.

In some embodiments, a glass-ceramic precursor glass composition comprises a source of: 50 to 75 wt. % $SiO_2$, 1 to 5 wt. % $Al_2O_3$, 0.5 to 10 wt. % $P_2O_5$, 1 to 15 wt. % CaO, 5 to 20 wt. % $Li_2O$, 0 to 5 wt. % $Na_2O$, 0.5 to 20 wt. % $ZrO_2$, and 0.1 to 1.0 wt. % $F^-$, based on a 100 wt. % total of the composition.

In some embodiments, a method of making a glass-ceramic composition comprises: ceramming a precursor glass mixture comprising a source of: 50 to 75 wt. % $SiO_2$, 1 to 5 wt. % $Al_2O_3$, 0.5 to 10 wt. % $P_2O_5$, 1 to 15 wt. % CaO, 5 to 20 wt. % $Li_2O$, 0 to 5 wt. % $Na_2O$, 0.5 to 20 wt. % $ZrO_2$, and 0.1 to 1.0 wt. % $F^-$, based on a 100 wt. % total of the composition, by heating the mixture at 600 to 800° C. for 0.5 to 10 hrs, and then heating at 850 to 950° C. for 0.5 to 20 hrs.

In one aspect, which is combinable with any of the other aspects or embodiments, the method further comprises: ion exchanging the resulting glass-ceramic composition to create at least one compressive stress layer on at least one surface of the article to increase mechanical strength.

In some embodiments, a bioactive composition comprises: a glass-ceramic composition comprising: a first crystalline phase including lithium disilicate; a second crystalline phase comprising at least one of: zircon, zirconia, apatite, or a combination thereof; and at least one live osteoblast cell.

In one aspect, which is combinable with any of the other aspects or embodiments, the glass-ceramic composition comprises a source of: 50 to 75 wt. % $SiO_2$, 1 to 5 wt. % $Al_2O_3$, 0.5 to 10 wt. % $P_2O_5$, 1 to 15 wt. % CaO, 5 to 20 wt. % $Li_2O$, 0 to 5 wt. % $Na_2O$, 0.5 to 20 wt. % $ZrO_2$, and 0.1 to 1.0 wt. % $F^-$, based on a 100 wt. % total of the composition.

In one aspect, which is combinable with any of the other aspects or embodiments, the bioactive composition further comprises a source of: 0 to 10 wt. % $B_2O_3$, and 0 to 4 wt. % $K_2O$, based on a 100 wt. % total of the composition.

In one aspect, which is combinable with any of the other aspects or embodiments, the glass-ceramic composition comprises a source of: 55 to 70 wt. % $SiO_2$, 1 to 3 wt. % $Al_2O_3$, 2 to 6 wt. % $P_2O_5$, 4 to 8 wt. % CaO, 10 to 15 wt. % $Li_2O$, 0.1 to 1 wt. % $Na_2O$, 3 to 15 wt. % $ZrO_2$, and 0.2 to 0.8 wt. % $F^-$, based on a 100 wt. % total of the composition.

In one aspect, which is combinable with any of the other aspects or embodiments, the bioactive composition further comprises a source of: 0 to 10 wt. % $B_2O_3$, and 0 to 4 wt. % $K_2O$, based on a 100 wt. % total of the composition.

In some embodiments, a method of culturing osteoblast cells comprises: contacting a bioactive composition described herein with a suitable liquid medium, wherein the contacting is configured to produce a proliferation of the osteoblast cells on a surface of the bioactive composition.

In one aspect, which is combinable with any of the other aspects or embodiments, the suitable liquid medium includes a simulated body fluid composition.

BRIEF DESCRIPTION OF THE DRAWINGS

The disclosure will become more fully understood from the following detailed description, taken in conjunction with the accompanying figures, in which.

DETAILED DESCRIPTION

Figure 1:
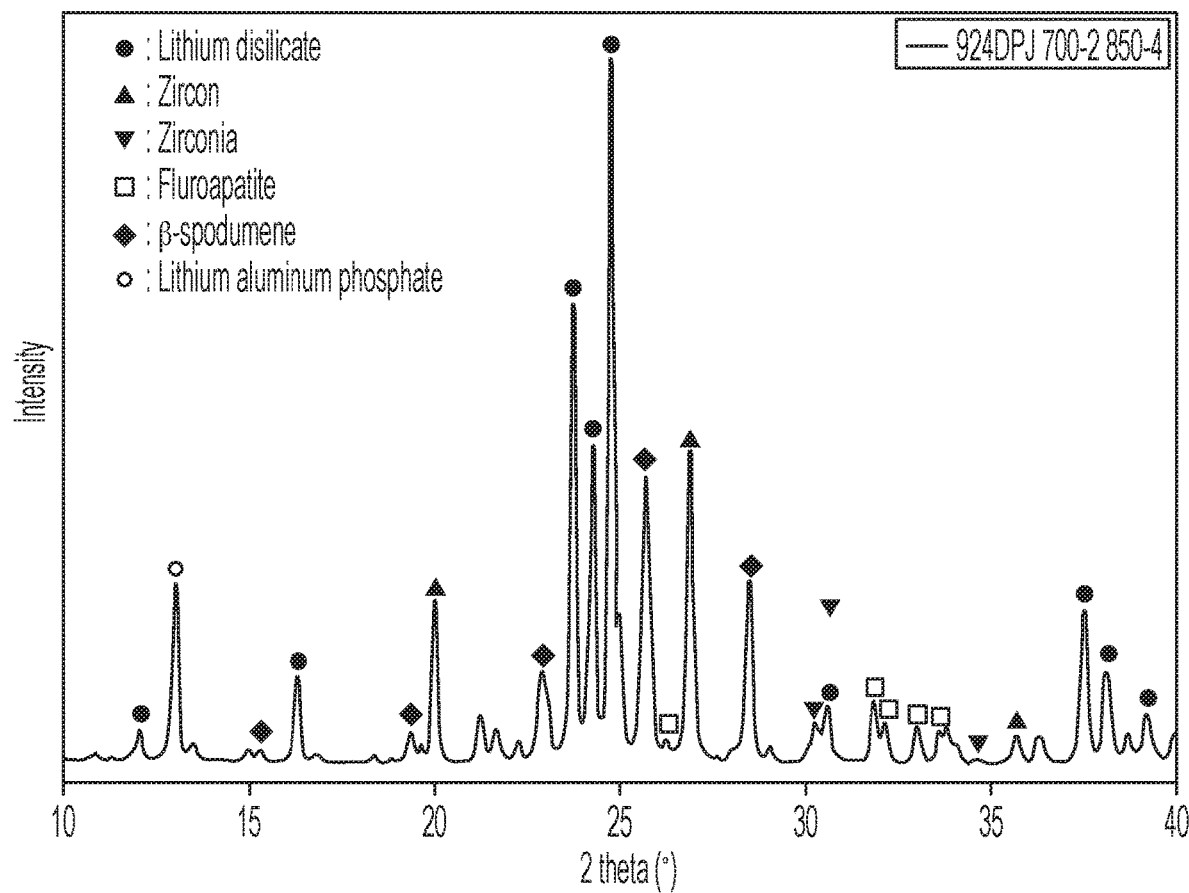
FIG. 1 illustrates an X-ray diffraction plot of a typical phase assemblage of Example composition 2 cerammed using a cycle of 700° C. for 2 hrs followed by 850° C. for 4 hrs, with a ramp rate of 5° C./min.

Reference will now be made in detail to exemplary embodiments which are illustrated in the accompanying drawings. Whenever possible, the same reference numerals will be used throughout the drawings to refer to the same or like parts. The components in the drawings are not necessarily to scale, emphasis instead being placed upon illustrating the principles of the exemplary embodiments. It should be understood that the present application is not limited to the details or methodology set forth in the description or illustrated in the figures. It should also be understood that the terminology is for the purpose of description only and should not be regarded as limiting.

Additionally, any examples set forth in this specification are illustrative, but not limiting, and merely set forth some of the many possible embodiments of the claimed invention. Other suitable modifications and adaptations of the variety of conditions and parameters normally encountered in the field, and which would be apparent to those skilled in the art, are within the spirit and scope of the disclosure.

Definitions

"Glass," "glasses," or like terms can refer to a glass or a glass-ceramic.

"Glass article," or like terms can refer to any object made wholly or partly of any of the disclosed glass or glass-ceramic compositions.

"Bioactivity Index," "index of bioactivity," "bioactivity," "$I_B$," or like terms or symbols refer to, for example, the time for more than 50% of the interface of a specific bioactive material to be bonded by a biological material such as bone, tissue, and like materials. Mathematically, a bioactivity index (according to Hench; see Cao, W., et al., Bioactive Materials, Ceramics International, 22 (1996) 493-507) is, $I_B=100/t_{0.5bb}$, where $t_{0.5bb}$ is the time for more than 50% of a bioactive material's interface, such as an implant, to be bonded by a biological material such as bone, tissue, and like materials, including osteoproductive (Class A having both intracellular and extracellular responses, e.g., 45S5 Bioglass®) and osteoconductive (Class B extracellular response only at interface, e.g., synthetic hydroxyapatite) materials.

Specific and preferred values disclosed for components, ingredients, additives, dimensions, conditions, times, and like aspects, and ranges thereof, are for illustration only; they do not exclude other defined values or other values within defined ranges. The composition and methods of the disclosure can include any value or any combination of the values, specific values, more specific values, and preferred values described herein, including explicit or implicit intermediate values and ranges.

Bioactive materials having high strength and toughness are in significant demand, for example, for the regeneration of bone and teeth.

In one example, lithium disilicate, $Li_2Si_2O_5$, is an orthorhombic crystal based on corrugated sheets of $Si_2O_5$ tetrahedral arrays. These crystals are typically tabular or lath-like in shape, with pronounced cleavage planes. Glass-ceramics based on lithium disilicate offer highly desirable mechanical properties, including high body strength and fracture toughness, due to their microstructures of randomly-oriented interlocking crystals. Glass-ceramics having fracture toughness values of 2 to 3 MPa·m$^{1/2}$ are achievable in the system of glass-ceramics based on lithium disilicate compositions disclosed herein.

Hydroxyapatite, $Ca_{10}(PO_4)_6(OH)_2$, is a naturally occurring mineral of biological and agricultural importance, the inorganic component in human and animal bones. It is biocompatible with bone and may be used for orthopedic and dental implants. Monoclinic $ZrO_2$ (baddeleyite) is a geological mineral with monoclinic-tetragonal-cubic phase transitions and may be used to stabilize tetragonal $ZrO_2$ ceramics. Structural ceramics based on stabilized $ZrO_2$ have excellent mechanical performance attributed to a combination of multiple toughening mechanisms. Due to its high strength and toughness (resulting from tetragonal to cubic phase transformation), $ZrO_2$ may be used as advanced functional or structural ceramics in dentistry, electronics and grinding industry. Zircon, $ZrSiO_4$, is a structural ceramic material with excellent chemical stability and corrosion resistance.

In some embodiments, novel glass-ceramic compositions are disclosed which produce multiple phases, including: lithium disilicate, zircon, zirconia and apatite in one system. The resulting glass-ceramic articles comprise interlocking lithium silicate with Zr-rich phases distributing between the grain boundary, thereby having high fracture toughness. Furthermore, the presence of apatite phase ensures biocompability for wide biomedical applications. In other words, in some embodiments, novel glass-ceramic compositions comprise a phase assemblage containing a major phase of lithium disilicate and a minor phase or phases of, for example, Zr-rich materials (e.g., zircon, zirconia, etc.) or apatite. These superior compositions exhibit an excellent combination of high mechanical strength and high bioactivity, which makes them excellent for hard tissue regeneration.

In some embodiments, a glass-ceramic composition comprises a first crystalline phase including lithium disilicate; and a second crystalline phase comprising at least one of: zircon, zirconia, apatite, or a combination thereof. In some examples, the second crystalline phase further comprises at least one of: β-spodumene, β-quartz, lithium aluminum phosphate, lithiophosphate, wollastonite, cristobalite, or a combination thereof. In some examples, the apatite comprises at least one of: fluorapatite, hydroxyapatite, carbonated apatite, or a combination thereof. In some examples, the first crystalline phase and the second crystalline phase, in combination, comprise a source of: 50 to 75 wt. % $SiO_2$, 1 to 5 wt. % $Al_2O_3$, 0.5 to 10 wt. % $P_2O_5$, 1 to 15 wt. % CaO, 5 to 20 wt. % $Li_2O$, 0 to 5 wt. % $Na_2O$, 0.5 to 20 wt. % $ZrO_2$, and 0.1 to 1.0 wt. % $F^-$, based on a 100 wt. % total of the composition. In some examples, the first crystalline phase and the second crystalline phase, in combination, comprise a source of: 55 to 70 wt. % $SiO_2$, 1 to 3 wt. % $Al_2O_3$, 2 to 6 wt. % $P_2O_5$, 4 to 8 wt. % CaO, 10 to 15 wt. % $Li_2O$, 0.1 to 1 wt. % $Na_2O$, 3 to 15 wt. % $ZrO_2$, and 0.2 to 0.8 wt. % $F^-$, based on a 100 wt. % total of the composition. In some examples, the first crystalline phase and the second crystalline phase, in combination, further comprise a source of: 0 to 10 wt. % $B_2O_3$, and 0 to 4 wt. % $K_2O$, based on a 100 wt. % total of the composition.

In some embodiments, a method of making a glass-ceramic composition comprises ceramming a precursor glass mixture comprising a source of: 50 to 75 wt. % $SiO_2$, 1 to 5 wt. % $Al_2O_3$, 0.5 to 10 wt. % $P_2O_5$, 1 to 15 wt. % CaO, 5 to 20 wt. % $Li_2O$, 0 to 5 wt. % $Na_2O$, 0.5 to 20 wt. % $ZrO_2$, and 0.1 to 1.0 wt. % $F^-$, based on a 100 wt. % total of the composition. In some examples, the ceramming comprises a first heating at a temperature in a range of 600 to 800° C. for 0.5 to 10 hrs, and a second heating at a temperature in a range of 850 to 950° C. for 0.5 to 20 hrs. In some examples, the cerammed precursor glass mixture may have a high crystallinity of at least 50%, or at least 55%, or at least 60%, or at least 65%, or at least 70%, or at least 75%, or at least 80%, or at least 85%, or at least 90%, or at least 95%, or at least 99%, or any value therebetween.

In some examples, the first heating may be conducted at a temperature of 610° C., or 620° C., or 630° C., or 640° C., or 650° C., or 660° C., or 670° C., or 680° C., or 690° C., or 700° C., or 710° C., or 720° C., or 730° C., or 740° C., or 750° C., or 760° C., or 770° C., or 780° C., or 790° C., or 800° C., or any temperature therebetween. In some examples, the first heating may be conducted at a temperature in a range of 625° C. to 775° C., or in a range of 650° C. to 750° C., or in a range of 675° C. to 725° C., or in a range of 685° C. to 715° C. In some examples, the first heating may be conducted for a time in a range of 0.5 hr, or 1.0 hr, or 1.5 hrs, or 2.0 hrs, or 2.5 hrs, or 3.0 hrs, or 3.5 hrs, or 4.0 hrs, or 4.5 hrs, or 5.0 hrs, or 5.5 hrs, or 6.0 hrs, or 6.5 hrs, or 7.0 hrs, or 7.5 hrs, or 8.0 hrs, or 8.5 hrs, or 9.0 hrs, or 9.5 hrs, or 10.0 hrs, or any time therebetween. In some examples, the first heating may be conducted at a time in a range of 0.5 hr to 8.0 hrs, or in a range of 0.5 hr to 6.0 hrs, or in a range of 0.5 hr to 5.0 hrs, or in a range of 1.0 hr to 4.0 hrs, or in a range of 1.5 hrs to 3.0 hrs.

In some examples, the second heating may be conducted at a temperature of 850° C., or 855° C., or 860° C., or 865° C., or 870° C., or 875° C., or 880° C., or 885° C., or 890° C., or 895° C., or 900° C., or 905° C., or 910° C., or 915° C., or 920° C., or 925° C., or 930° C., or 935° C., or 940° C., or 945° C., or 950° C., or any temperature therebetween. In some examples, the second heating may be conducted at a temperature in a range of 860° C. to 940° C., or in a range of 870° C. to 920° C., or in a range of 870° C. to 900° C., or in a range of 900° C. to 950° C. In some examples, the second heating may be conducted for a time in a range of 0.5 hr, or 1.0 hr, or 1.5 hrs, or 2.0 hrs, or 2.5 hrs, or 3.0 hrs, or 3.5 hrs, or 4.0 hrs, or 4.5 hrs, or 5.0 hrs, or 5.5 hrs, or 6.0 hrs, or 6.5 hrs, or 7.0 hrs, or 7.5 hrs, or 8.0 hrs, or 8.5 hrs, or 9.0 hrs, or 9.5 hrs, or 10.0 hrs, or 10.5 hrs, or 11.0 hrs, or 11.5 hrs, or 12.0 hrs, or 12.5 hrs, or 13.0 hrs, or 13.5 hrs, or 14.0 hrs, or 14.5 hrs, or 15.0 hrs, or 15.5 hrs, or 16.0 hrs, or 16.5 hrs, or 17.0 hrs, or 17.5 hrs, or 18.0 hrs, or 18.5 hrs, or 19.0 hrs, or 19.5 hrs, or 20.0 hrs, any time therebetween. In some examples, the second heating may be conducted at a time in a range of 0.5 hr to 10 hrs, or in a range of 0.5 hr to 8 hrs, or in a range of 1.0 hr to 8 hrs, or in a range of 1.0 hr to 5 hrs, or in a range of 2.0 hrs to 5.0 hrs.

Table 1 describes examples of the precursor glass mixture, ceramming conditions thereof, and physical characteristics.

TABLE 1

| Example Composition (wt %) | 1 | 2 | 3 | 4 | 5 | 6 |
|---|---|---|---|---|---|---|
| $SiO_2$ | 67.6 | 66.2 | 64.8 | 63.4 | 62.1 | 60.9 |
| $Al_2O_3$ | 2.8 | 2.7 | 2.7 | 2.6 | 2.5 | 2.5 |
| $Li_2O$ | 13.3 | 13.0 | 12.7 | 12.5 | 12.2 | 12.0 |
| $Na_2O$ | 0.2 | 0.2 | 0.2 | 0.2 | 0.2 | 0.2 |
| CaO | 6.7 | 6.5 | 6.4 | 6.2 | 6.1 | 6.0 |
| $P_2O_5$ | 4.4 | 4.3 | 4.2 | 4.2 | 4.1 | 4.0 |
| $ZrO_2$ | 4.4 | 6.5 | 8.5 | 10.4 | 12.2 | 14.0 |
| F— | 0.6 | 0.5 | 0.5 | 0.5 | 0.5 | 0.5 |
| Ceramming | | | | | | |
| First heating | | | 700° C. for 2 hrs | | | |
| Second heating | | | 875° C. for 4 hrs | | | |
| Phase assemblage | | | Lithium disilicate Zircon $ZrO_2$ β-spodumene Fluorapatite | | | |
| Appearance | N/A | | lithium aluminum phosphate White opaque | | | |
| Fracture toughness (MPa · $m^{1/2}$) | N/A | 2.4 | 3.1 | 2.6 | 2.4 | N/A |

Although not bound by theory, it is believed that the presence of interlocking crystals is a factor in developing toughening mechanisms including, for example, crack deflection and tortuous crack path, which contribute to the observed high fracture toughness and high flexural strength.

As exemplified by Example Compositions 1 to 6, the composition may have a high fracture toughness in a range of 2.0 to 3.5 MPa·$m^{1/2}$, or in a range of 2.2 to 3.3 MPa·$m^{1/2}$, or in a range of 2.4 to 3.1 MPa·$m^{1/2}$, or any range therebetween. In some examples, the composition may have a high fracture toughness of at least 2.0 MPa·$m^{1/2}$, or at least 2.1 MPa·$m^{1/2}$, or at least 2.2 MPa·$m^{1/2}$, or at least 2.3 MPa·$m^{1/2}$, or at least 2.4 MPa·$m^{1/2}$, or at least 2.5 MPa·$m^{1/2}$, or at least 2.6 MPa·$m^{1/2}$, or at least 2.7 MPa·$m^{1/2}$, or at least 2.8 MPa·$m^{1/2}$, or at least 2.9 MPa·$m^{1/2}$, or at least 3.0 MPa·$m^{1/2}$, or at least 3.1 MPa·$m^{1/2}$, or at least 3.2 MPa·$m^{1/2}$, or at least 3.3 MPa·$m^{1/2}$, or at least 3.4 MPa·$m^{1/2}$, or at least 3.5 MPa·$m^{1/2}$, or any value therebetween.

The composition may have a high strength in a range of 200 to 500 MPa, or in a range of 250 to 400 MPa, or in a range of 300 to 400 MPa, or any range therebetween. In some examples, the composition may have a high strength in a range of at least 200 MPa, or at least 220 MPa, or at least 240 MPa, or at least 260 MPa, or at least 280 MPa, or at least 300 MPa, or at least 320 MPa, or at least 340 MPa, or at least 360 MPa, or at least 380 MPa, or at least 400 MPa, or at least 420 MPa, or at least 440 MPa, or at least 460 MPa, or at least 480 MPa, or at least 500 MPa, or any value therebetween.

Referring to FIG. 1, an X-ray diffraction plot of the phase assemblage of Example Composition 2 is shown cerammed using a cycle of 700° C. for 2 hrs followed by 850° C. for 4 hrs, with a ramp rate of 5° C./min. Powder X-ray diffraction results were collected using a Bruker X-ray diffractometer. Multiple crystalline phases including lithium disilicate, zircon, zirconia and fluorapatite are observed, as well as other phases such as β-spodumene and lithium aluminum phosphate. The apatite phase, for example, is an inorganic component of biological bone and teeth, thereby ensuring good biocompatibility of the glass-ceramic compositions disclosed herein for biomedical applications.

Figure 2A:
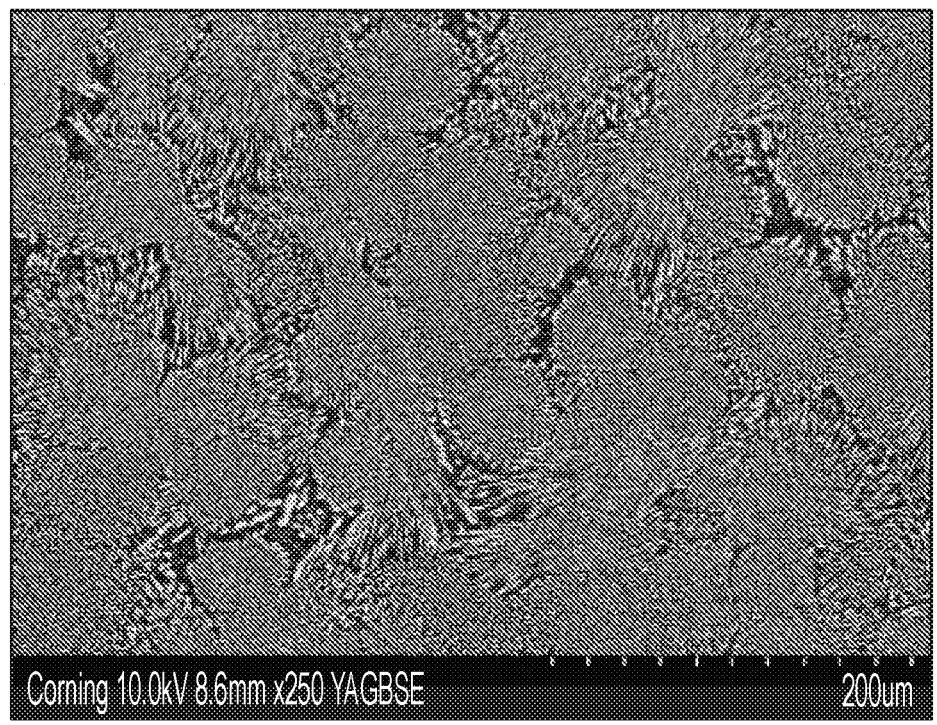
FIGS. 2A to 2D illustrate scanning electron microscopy (SEM) images of the microstructure of a phase assemblage of Example composition 2 cerammed using a cycle of 700° C. for 2 hrs followed by 850° C. for 4 hrs, with a ramp rate of 5° C./min. For all images, a 10.0 kV beam accelerating voltage was utilized. The microstructures are shown at: 250× magnification and 200 μm scale (FIG. 2A); 1000× magnification and 50.0 μm scale (FIG. 2B); 2500× magnification and 20.0 μm scale (FIG. 2C); and 10000× magnification and 5.0 μm scale (FIG. 2D).
Figure 2B:
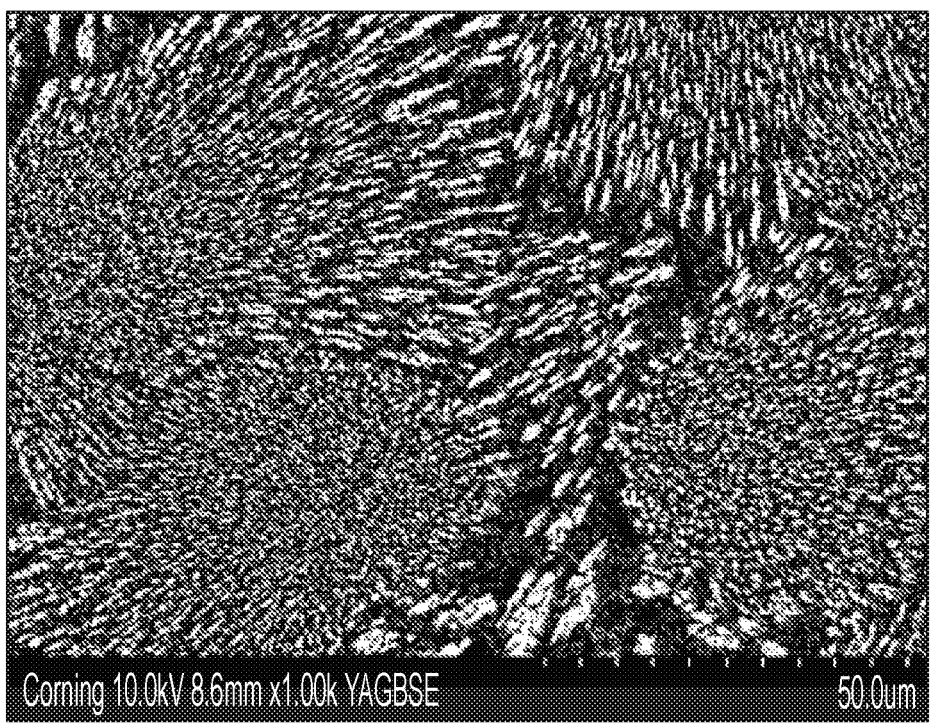
Figure 2C:
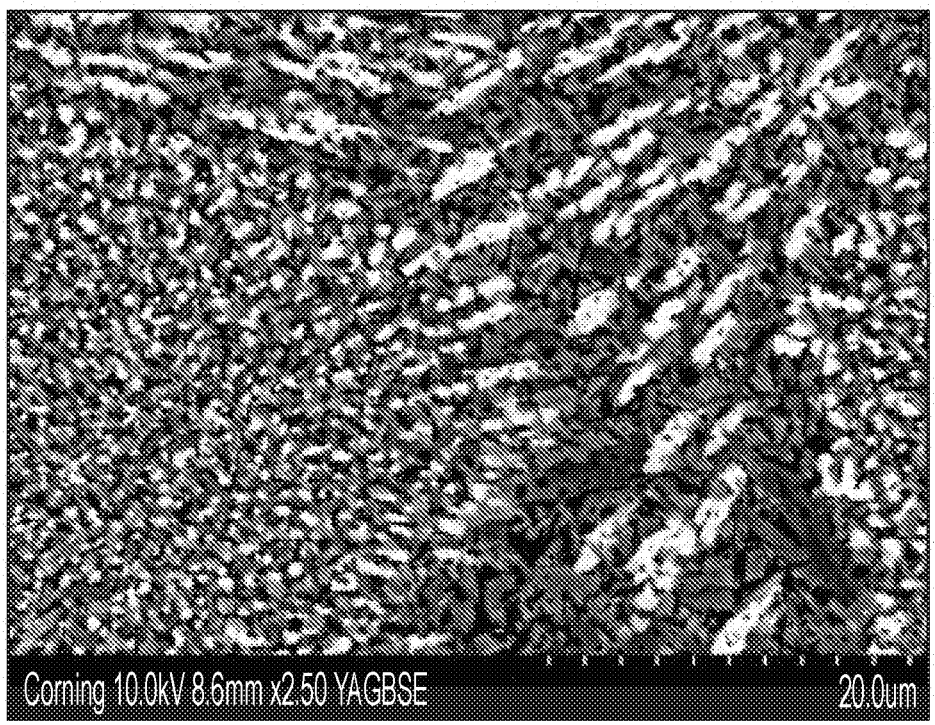
Figure 2D:
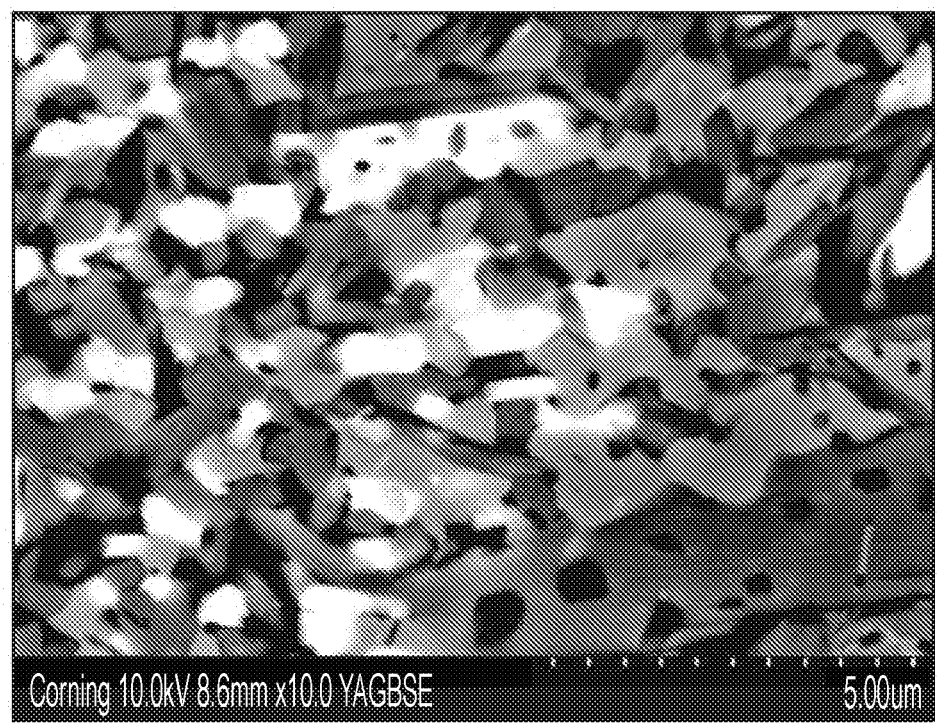

Referring to FIGS. 2A to 2D, SEM images of the microstructure of the phase assemblage of Example Composition 2 is shown. For all images, a 10.0 kV beam accelerating voltage was utilized. The microstructures are shown at: 250× magnification and 200 μm scale (FIG. 2A); 1000× magnification and 50.0 μm scale (FIG. 2B); 2500× magnification and 20.0 μm scale (FIG. 2C); and 10000× magnification and 5.0 μm scale (FIG. 2D). A Hitachi SEM was used to observe the microstructure in polished cross sections. The white spots correspond to Zr-rich phases and the acicular needles to lithium disilicate.

As explained above, glass-ceramic articles comprising interlocking lithium disilicate may be obtained by ceramming precursor glasses at temperatures in a range of 600° C. to 1000° C. for predetermined times. As seen in FIGS. 2A to 2D, the white Zr-rich phase is distributed at the acicular needle lithium disilicate grain boundaries. The presence of interlocking crystals from multiple crystals (e.g., lithium disilicate, zircon, zirconia, fluorapatite, β-spodumene, and lithium aluminum phosphate for Example Composition 2, for example) is important for developing toughening mechanisms including, for example, crack deflection and tortuous crack path, which contribute to the observed high fracture toughness and high flexural strength.

In some examples, after the step of ceramming, the method further comprises ion exchanging the resulting glass-ceramic composition to create at least one compressive stress layer on at least one surface of the article to increase mechanical strength.

In some examples, the disclosed glass-ceramics may be manufactured using a thin rolling, a float, a casting process, and like methods; and scaffolds can be produced using, for example, rapid prototyping, polymer foam replication, particle sintering, and like methods. Glass-ceramics of desired forms can be used to support cell growth and hard tissue regeneration.

Mechanical strength, biocompatibility and degradation are influenced by glass compositions. In the glass compositions described herein, $SiO_2$ serves as a primary glass-forming oxide for precursor glass and may function to stabilize the networking structure of glass and glass-ceramics. The concentration of $SiO_2$ should be sufficiently high (e.g., greater than 50 wt. %) to form lithium disilicate crystal phase when the precursor glass is heat-treated to convert to a glass-ceramic (cerammed). However, glasses containing too much $SiO_2$ (e.g., greater than 75 wt. % $SiO_2$) often suffer from undesirably high melting temperature (200 poise temperature of pure $SiO_2$ or high-$SiO_2$ glasses). In some examples, glass or glass-ceramic compositions comprise 50 wt. % to 75 wt. % $SiO_2$.

Alumina (e.g., $Al_2O_3$) may also provide stabilization to the networking structure and is favorable to improvement of mechanical properties and chemical durability. Too high a content of $Al_2O_3$ (e.g., greater than 5 wt. %) generally increases viscosity of the melt and decreases the fraction of lithium disilicate crystals such that no interlocking structure is formed. In some examples, $Al_2O_3$ concentration is controlled in a range of 1 wt. % to 5 wt. %.

Zirconium dioxide (e.g., $ZrO_2$) may function as a network former or intermediate in precursor glasses, as well as helping to improve stability in Li-based glasses (e.g., $Li_2O$—$Al_2O_3$—$SiO_2$—$P_2O_5$) by significantly reducing glass devitrification during forming and lowering liquidus temperature. Clear patties may be formed from glasses containing over 0.5 wt. % $ZrO_2$, with no liquidus concerns at $ZrO_2$ concentrations in a range of 0.5 wt. % to 20 wt. %. The presence of crystalline $ZrO_2$ and zircon phases is beneficial for achieving white colorations and high fracture toughness. Moreover, $ZrO_2$ is also believed to increase chemical durability of the glass-ceramics.

Lithium dioxide (e.g., $Li_2O$) is another important component in the precursor glass composition for forming of lithium disilicate crystal phases. At concentrations below 5 wt. %, the resultant glass-ceramic would not include lithium disilicate as the predominant phase, which is needed to achieve the properties described herein. At concentrations above 20 wt. %, the $Li_2O$ content is too high, with the precursor glasses becoming very fluid with low resistivity, thereby making it difficult to melt or form.

The compositions disclosed herein also include $P_2O_5$ to serve as a nucleating agent for bulk nucleation. If the concentration of $P_2O_5$ is too low (e.g., less than 0.5 wt. %), the precursor glass does not crystallize. However, if the concentration is too high (e.g., greater than 10 wt. %), the devitrification, upon cooling during precursor glass forming, may be difficult to control.

Other elements of the composition may include divalent cation oxides (such as alkaline earth oxides) to improve melting behavior and bioactivity of the glass. For example, calcium oxide (CaO) is found to combine with $P_2O_5$ to form apatite, which is a bioactive ceramic. Inclusion of monovalent cation oxides (such as alkali earth oxides, e.g., $Na_2O$, and optionally, $K_2O$), helps to reduce melting temperature of the glass as well as shorten the ceramming cycle. Furthermore, $Na_2O$ and $K_2O$ may also increase thermal expansion after ceramming if a higher thermal expansion is desired in the glass-ceramic articles. Boron trioxide ($B_2O_3$) may optionally be included as beneficial to crack resistance of the glass-ceramics, which is helpful for dental applications. Furthermore, higher boron concentrations (5 wt. % to 10 wt. %) can increase their degradation rate of the bulk material, which may be desired for applications in bone regeneration.

In some examples, the disclosed compositions may be free of (e.g., zero ppm or ppb), or substantially free of (e.g., trace amounts less than several ppm or ppb), at least one of, for example, $K_2O$, $K_2CO_3$, $Ca_3(PO_4)_2$, MgO, $TiO_2$, $As_2O_3$, $Sb_2O_3$, or combinations or mixtures thereof Bioactive Compositions In some embodiments, a bioactive composition comprises a glass-ceramic composition with a first crystalline phase including lithium disilicate; a second crystalline phase comprising at least one of zircon, zirconia, apatite, or a combination thereof; and at least one live osteoblast cell, that is, a bioactive glass-ceramic including compositions disclosed herein and cells capable of synthesizing bone.

In some examples, the glass-ceramic composition comprises a source of 50 to 75 wt. % $SiO_2$, 1 to 10 wt. % $Al_2O_3$, 1 to 10 wt. % $P_2O_5$, 1 to 15 wt. % CaO, 5 to 20 wt. % $Li_2O$, 0 to 5 wt. % $Na_2O$, 1 to 20 wt. % $ZrO_2$, and 0.1 to 1.0 wt. % $F^-$, based on a 100 wt. % total of the composition. In some examples, the glass-ceramic composition comprises a source of: 55 to 70 wt. % $SiO_2$, 1 to 3 wt. % $Al_2O_3$, 2 to 6 wt. %

$P_2O_5$, 4 to 8 wt. % CaO, 10 to 15 wt. % $Li_2O$, 0.1 to 1 wt. % $Na_2O$, 3 to 15 wt. % $ZrO_2$, and 0.2 to 0.8 wt. % $F^-$, based on a 100 wt. % total of the composition. In some examples, the bioactive composition further comprises a source of: 0 to 10 wt. % $B_2O_3$, and 0 to 4 wt. % $K_2O$, based on a 100 wt. % total of the composition.

In some examples, a method of culturing osteoblast cells includes contacting a bioactive composition described herein with a suitable liquid medium, such that the contacting produces a proliferation of the osteoblast cells on a surface of the bioactive composition or in the suitable liquid medium (such as the culture medium of MC3T3 cells: i.e., alpha-MEM supplemented with 10% fetal bovine serum and 1 mM sodium pyruvate).

In some examples, the suitable liquid medium can include, for example, a simulated body fluid (SBF) composition. SBF may be used for testing apatite formation activity of bioactive glasses/glass-ceramics. The disclosed bioactive glass-ceramics form in-situ a biologically active apatite layer (e.g., the mineral phase of bone and teeth) that can bond to bone, teeth, and even soft tissue. In embodiments, the disclosed compositions are biocompatible with various cell types in various applications, and are biologically active (i.e., bioactive). The potential applications of the disclosed bioactive glass-ceramics can include, for example, monolithic articles, composites, films, coating, or like forms, for use in repair of load-bearing bones, dental regeneration, treatment of dental hypersensitivity, artificial vertebrae, spinous spacers, intervertebral spacers, iliac spacers, granular fillers, scaffolds, middle-ear implant and in other types of small-bone replacement, wound healing (keratinocytes), bone tissue engineering (MC3T3 cells), angiogenesis, and like applications. The disclosed bioactive glass-ceramics are biocompatible with, for example, osteoblasts, keratinocytes, human umbilical vein endothelial cells (HUVEC), etc.

In some examples, the disclosed bioactive glass-ceramic compositions may further comprise, for example, a form factor selected from: a hollow microsphere, a solid microsphere, or combinations thereof, that is, where the glass composition has a particle shape, such as a sphere, an elongated sphere or egg-shape, a rod, or like geometries.

Advantages of the disclosed glass-ceramic compositions disclosed herein include: (1) a unique phase assemblage by producing multiple known tough phases in a single system; (2) interlocking microstructures embedded with Zr-rich crystalline phases to produce a high fracture toughness and high strength; (3) inclusion of a fluoroapatite ensuring excellent biocompatibility for biomedical (e.g., dental) applications; and (4) a capability of supporting growth and functionalization of osteoblastic cells.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the invention as recited in the appended claims.

As utilized herein, "optional," "optionally," or the like are intended to mean that the subsequently described event or circumstance can or cannot occur, and that the description includes instances where the event or circumstance occurs and instances where it does not occur. The indefinite article "a" or "an" and its corresponding definite article "the" as used herein means at least one, or one or more, unless specified otherwise.

References herein to the positions of elements (e.g., "top," "bottom," "above," "below," etc.) are merely used to describe the orientation of various elements in the FIGURES. It should be noted that the orientation of various elements may differ according to other exemplary embodiments, and that such variations are intended to be encompassed by the present disclosure.

With respect to the use of substantially any plural and/or singular terms herein, those having skill in the art can translate from the plural to the singular and/or from the singular to the plural as is appropriate to the context and/or application. The various singular/plural permutations may be expressly set forth herein for the sake of clarity.

It will be apparent to those skilled in the art that various modifications and variations can be made without departing from the spirit or scope of the claimed subject matter. Accordingly, the claimed subject matter is not to be restricted except in light of the attached claims and their equivalents.

What is claimed is:

1. A glass-ceramic composition, comprising:
   a first crystalline phase including lithium disilicate; and
   a second crystalline phase comprising zircon, zirconia, and apatite.

2. The glass-ceramic composition of claim 1, wherein the second crystalline phase further comprises at least one of: β-spodumene, β-quartz, lithium aluminum phosphate, lithiophosphate, wollastonite, cristobalite, or a combination thereof.

3. The glass-ceramic composition of claim 1, wherein the apatite comprises at least one of: fluorapatite, hydroxyapatite, carbonated apatite, or a combination thereof.

4. The glass-ceramic composition of claim 1, wherein the first crystalline phase and the second crystalline phase, in combination, comprise a source of:
   50 to 75 wt. % $SiO_2$,
   1 to 5 wt. % $Al_2O_3$,
   0.5 to 10 wt. % $P_2O_5$,
   1 to 15 wt. % CaO,
   5 to 20 wt. % $Li_2O$,
   0 to 5 wt. % $Na_2O$,
   0.5 to 20 wt. % $ZrO_2$, and
   0.1 to 1.0 wt. % F, based on a 100 wt. % total of the composition.

5. The glass-ceramic composition of claim 4, wherein the first crystalline phase and the second crystalline phase, in combination, further comprise a source of:
   0 to 10 wt. % $B_2O_3$, and
   0 to 4 wt. % $K_2O$, based on a 100 wt. % total of the composition.

6. The glass-ceramic composition of claim 1, wherein the composition has a high fracture toughness in a range of 2.0 to 3.5 $MPa \cdot m^{1/2}$.

7. The glass-ceramic composition of claim 1, wherein the composition has a flexural strength in a range of 200 to 500 MPa.

8. The glass-ceramic composition of claim 1, wherein the composition has a high fracture toughness in a range of 2.0 to 3.5 $MPa \cdot m^{1/2}$ and a flexural strength in a range of 200 to 500 MPa.

9. The glass-ceramic composition of claim 1, wherein the first crystalline phase and the second crystalline phase, in combination, comprise a source of:
55 to 70 wt. % $SiO_2$,
1 to 3 wt. % $Al_2O_3$,
2 to 6 wt. % $P_2O_5$,
4 to 8 wt. % CaO,
10 to 15 wt. % $Li_2O$,
0.1 to 1 wt. % $Na_2O$,
3 to 15 wt. % $ZrO_2$, and
0.2 to 0.8 wt. % F, based on a 100 wt. % total of the composition.

10. The glass-ceramic composition of claim 9, wherein the first crystalline phase and the second crystalline phase, in combination, further comprise a source of:
0 to 10 wt. % $B_2O_3$, and
0 to 4 wt. % $K_2O$, based on a 100 wt. % total of the composition.

11. A bioactive composition, comprising:
a glass-ceramic composition comprising:
a first crystalline phase including lithium disilicate;
a second crystalline phase comprising zircon, zirconia, and apatite; and
at least one live osteoblast cell.

12. The bioactive composition of claim 11, wherein the glass-ceramic composition comprises a source of:
50 to 75 wt. % $SiO_2$,
1 to 5 wt. % $Al_2O_3$,
0.5 to 10 wt. % $P_2O_5$,
1 to 15 wt. % CaO,
5 to 20 wt. % $Li_2O$,
0 to 5 wt. % $Na_2O$,
0.5 to 20 wt. % $ZrO_2$, and
0.1 to 1.0 wt. % F, based on a 100 wt. % total of the composition.

13. The bioactive composition of claim 12, further comprising a source of:
0 to 10 wt. % $B_2O_3$, and
0 to 4 wt. % $K_2O$, based on a 100 wt. % total of the composition.

14. The bioactive composition of claim 11, wherein the glass-ceramic composition comprises a source of:
55 to 70 wt. % $SiO_2$,
1 to 3 wt. % $Al_2O_3$,
2 to 6 wt. % $P_2O_5$,
4 to 8 wt. % CaO,
10 to 15 wt. % $Li_2O$,
0.1 to 1 wt. % $Na_2O$,
3 to 15 wt. % $ZrO_2$, and
0.2 to 0.8 wt. % F, based on a 100 wt. % total of the composition.

15. The bioactive composition of claim 14, further comprising a source of:
0 to 10 wt. % $B_2O_3$, and
0 to 4 wt. % $K_2O$, based on a 100 wt. % total of the composition.

16. A method of culturing osteoblast cells comprising:
contacting the bioactive composition of claim 11 with a suitable liquid medium, wherein the contacting is configured to produce a proliferation of the osteoblast cells on a surface of the bioactive composition.

17. The method of claim 16, wherein the suitable liquid medium includes a simulated body fluid composition.

18. The glass-ceramic composition of claim 4, wherein the source of the first crystalline phase and the second crystalline phase, in combination, comprises >0 to <0.4 wt. % $Na_2O$.

19. The glass-ceramic composition of claim 4, wherein the source of the first crystalline phase and the second crystalline phase, in combination, comprises 8.5 to 15 wt. % $ZrO_2$.

* * * * *